(12) United States Patent
Eckhouse et al.

(10) Patent No.: US 10,751,073 B2
(45) Date of Patent: Aug. 25, 2020

(54) CLOT REMOVAL DEVICE WITH STEERABLE ELEMENT

(71) Applicant: RAPID MEDICAL LTD., Yokneam (IL)

(72) Inventors: Ronen Eckhouse, Shimshit (IL); Yuri Sudin, Modiin (IL); Shimon Eckhouse, Haifa (IL)

(73) Assignee: Rapid Medical LTD, Yokneam (IL)

( * ) Notice: Subject to any disclaimer, the term of this patent is extended or adjusted under 35 U.S.C. 154(b) by 996 days.

(21) Appl. No.: 13/962,881

(22) Filed: Aug. 8, 2013

(65) Prior Publication Data

US 2013/0325056 A1 Dec. 5, 2013

Related U.S. Application Data

(63) Continuation-in-part of application No. 13/279,898, filed on Oct. 24, 2011, now Pat. No. 9,034,008, which
(Continued)

(51) Int. Cl.
*A61B 17/22* (2006.01)
*A61B 17/221* (2006.01)
(Continued)

(52) U.S. Cl.
CPC ........ *A61B 17/22031* (2013.01); *A61B 17/22* (2013.01); *A61B 17/221* (2013.01);
(Continued)

(58) Field of Classification Search
CPC . A61B 17/22; A61B 17/22031; A61B 17/221; A61B 2017/2215; A61B 2017/2217
See application file for complete search history.

(56) References Cited

U.S. PATENT DOCUMENTS

| 3,367,101 A | 2/1968 | Garner et al. |
| 3,435,826 A | 4/1969 | Fogarty |

(Continued)

FOREIGN PATENT DOCUMENTS

| EP | 0 820 729 A1 | 1/1998 |
| EP | 1 949 921 A2 | 7/2008 |

(Continued)

OTHER PUBLICATIONS

International Search Report and Written Opinion for PCT/IB2014/063783, dated Oct. 1, 2014, corresponding to U.S. Appl. No. 13/962,881 (12 pages total).

(Continued)

*Primary Examiner* — Sarah A Simpson
(74) *Attorney, Agent, or Firm* — Finnegan, Henderson, Farabow, Garrett & Dunner LLP

(57) ABSTRACT

A clot removal device and method for removing a clot from a blood vessel are provided, where the clot removal device includes a shaft and an elongate clot engagement element having one end connected to the shaft and a distal end remote from the end connected to the shaft, and where the shaft and elongate clot engagement element having a principal longitudinal axis. Further, the distal end can include an end formation forming a curved contact surface at the distal end, and the end formation can be displaced to one side of the principal longitudinal axis.

18 Claims, 14 Drawing Sheets

Related U.S. Application Data is a continuation-in-part of application No. 13/059,319, filed as application No. PCT/IL2009/000834 on Aug. 30, 2009, now abandoned.

(60) Provisional application No. 61/119,369, filed on Dec. 2, 2008, provisional application No. 61/093,173, filed on Aug. 29, 2008.

(51) Int. Cl.
*A61B 17/00* (2006.01)
*A61B 17/30* (2006.01)
*A61F 2/915* (2013.01)

(52) U.S. Cl.
CPC ............ *A61B 2017/00685* (2013.01); *A61B 2017/00867* (2013.01); *A61B 2017/2217* (2013.01); *A61B 2017/22034* (2013.01); *A61B 2017/306* (2013.01); *A61F 2/915* (2013.01)

(56) References Cited

U.S. PATENT DOCUMENTS

| | | | |
|---|---|---|---|
| 3,749,085 A * | 7/1973 | Willson | A61B 10/04 600/570 |
| 4,030,503 A | 6/1977 | Clark, III | |
| 4,403,612 A | 9/1983 | Fogarty | |
| 4,653,496 A * | 3/1987 | Bundy | A61B 17/3207 600/564 |
| 4,706,671 A * | 11/1987 | Weinrib | A61B 17/221 604/104 |
| 4,762,130 A | 8/1988 | Fogarty et al. | |
| 4,890,611 A | 1/1990 | Monfort et al. | |
| 5,011,488 A | 4/1991 | Ginsburg | |
| 5,112,347 A | 5/1992 | Taheri | |
| 5,192,286 A | 3/1993 | Phan et al. | |
| 5,411,509 A | 5/1995 | Hilal | |
| 5,490,859 A | 2/1996 | Mische et al. | |
| 5,695,519 A | 12/1997 | Summers et al. | |
| 5,772,674 A | 6/1998 | Nakhjavan | |
| 5,972,019 A | 10/1999 | Engelson et al. | |
| 6,096,053 A | 8/2000 | Bates | |
| 6,159,230 A | 12/2000 | Samuels | |
| 6,695,858 B1 | 2/2004 | Dubrul et al. | |
| 6,902,540 B2 | 6/2005 | Dorros et al. | |
| 7,041,116 B2 | 5/2006 | Goto et al. | |
| 7,326,220 B1 | 2/2008 | Goldstein | |
| 7,575,585 B2 | 8/2009 | Goto et al. | |
| 2001/0031980 A1 * | 10/2001 | Wensel | A61B 17/221 606/200 |
| 2002/0095169 A1 | 7/2002 | Maitland et al. | |
| 2002/0123765 A1 * | 9/2002 | Sepetka | A61B 17/22031 606/192 |
| 2002/0161393 A1 | 10/2002 | Demond et al. | |
| 2002/0161397 A1 * | 10/2002 | Mathews | A61B 17/221 606/200 |
| 2003/0191492 A1 | 10/2003 | Gellman et al. | |
| 2003/0236534 A1 | 12/2003 | Kayan | |
| 2005/0154400 A1 | 7/2005 | Kato et al. | |
| 2005/0228417 A1 * | 10/2005 | Teitelbaum | A61B 17/22031 606/159 |
| 2006/0195137 A1 | 8/2006 | Sepetka et al. | |
| 2007/0038241 A1 | 2/2007 | Pal | |
| 2007/0185501 A1 | 8/2007 | Martin et al. | |
| 2007/0208370 A1 | 9/2007 | Hauser et al. | |
| 2012/0041449 A1 | 2/2012 | Eckhouse et al. | |

FOREIGN PATENT DOCUMENTS

| | | |
|---|---|---|
| JP | S63-212338 A | 9/1988 |
| JP | 2003-10193 A | 1/2003 |
| JP | 2003-33359 A | 2/2003 |
| JP | 2008-520351 A | 6/2008 |
| JP | 2011-104388 A | 6/2011 |
| WO | WO 99/23952 | 5/1999 |
| WO | WO 99/60933 | 12/1999 |
| WO | WO 2008/057554 A1 | 5/2008 |
| WO | WO 2010/046897 A1 | 4/2010 |

OTHER PUBLICATIONS

International Search Report for PCT/IL2009/000834, dated Apr. 9, 2010, corresponding to U.S. Appl. No. 13/059,318 (5 pages total).

International Search Report for PCT/IL2009/000992, dated Mar. 4, 2010, corresponding to U.S. Appl. No. 13/125,324 (5 pages total).

USPTO Office Action dated Apr. 9, 2013, for U.S. Appl. No. 13/279,870, (7 pages total).

USPTO Office Action dated Apr. 21, 2013, for U.S. Appl. No. 13/125,324 (27 pages total).

Communication from European Patent Office in European Appl. EP 09 764 899 dated Aug. 22, 2012, corresponding to U.S. Appl. No. 13/125,324 (3 pages).

Communication from European Patent Office in European Appl. EP 10 191 770 dated Feb. 10, 2011, corresponding to U.S. Appl. No. 13/059,318 (4 pages total).

Chinese Office Action dated Aug. 17, 2017 and Search Report for Chinese Application No. 201480051579.2 (which corresponds to U.S. Appl. No. 13/962,881), and English translation thereof (15 pages total).

Chinese Office Action dated May 16, 2018, for Chinese Application No. 201480051579.2 (which corresponds to U.S. Appl. No. 13/962,881) and English translation thereof (7 pages total).

Japanese Office Action dated Jun. 7, 2018, for Japanese Application No. 2016-532784 (which corresponds to U.S. Appl. No. 13/962,881) and English translation thereof (6 pages total).

* cited by examiner

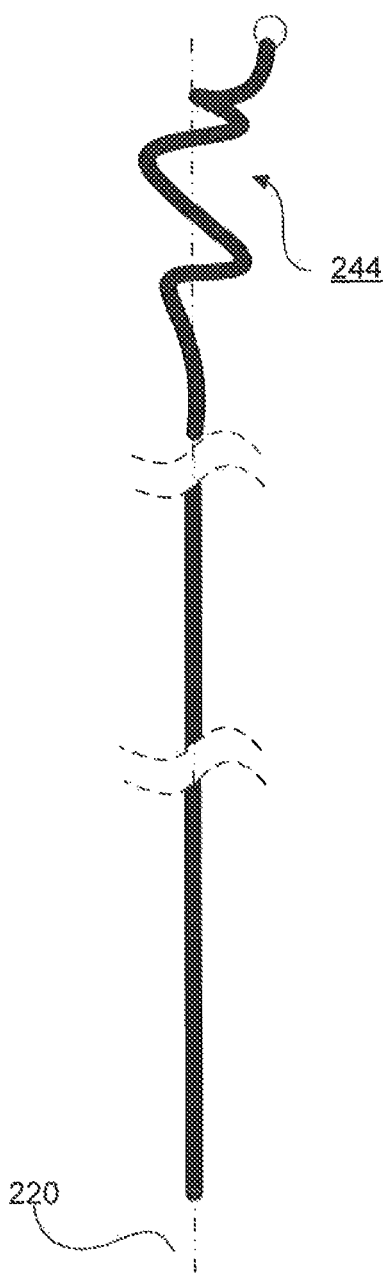 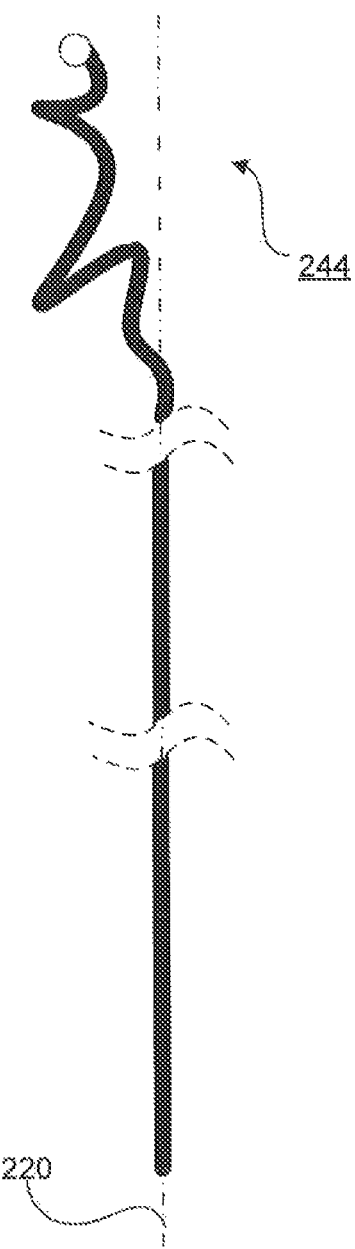
FIG. 12A  FIG. 12B

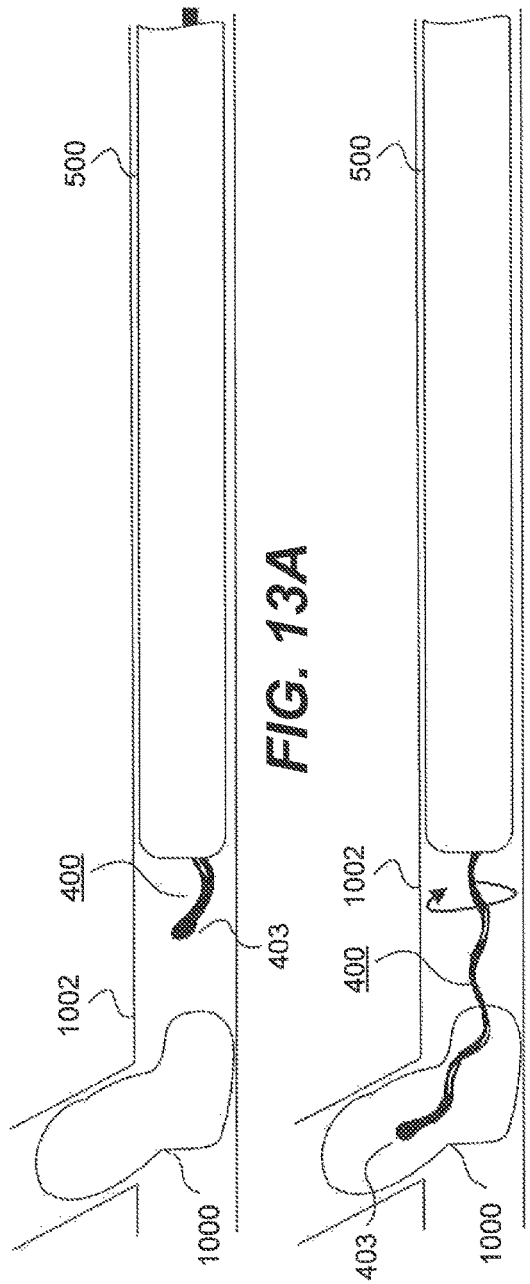
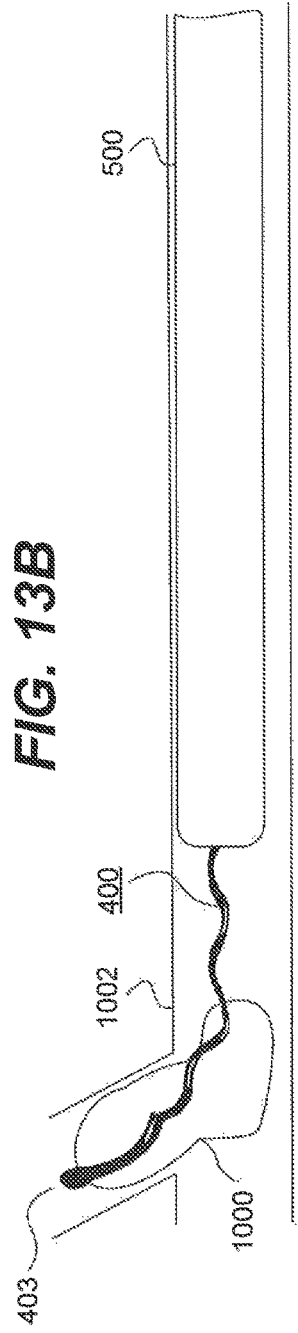
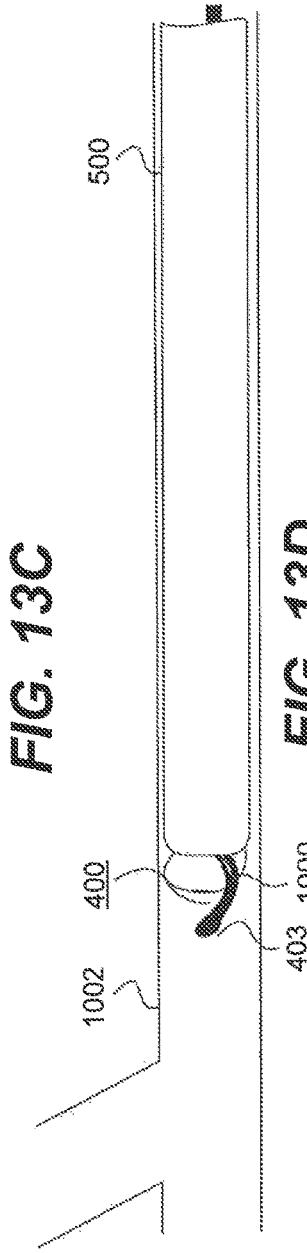
FIG. 13A
FIG. 13B
FIG. 13C
FIG. 13D

CLOT REMOVAL DEVICE WITH STEERABLE ELEMENT

CROSS-REFERENCE TO RELATED APPLICATIONS

This application is a continuation-in-part of U.S. patent application Ser. No. 13/279,898, filed on Oct. 24, 2011, entitled "Device and Method Involving Stabilization During Clot Removal," which is a continuation-in-part of U.S. patent application Ser. No. 13/059,319, filed on Feb. 16, 2011, entitled "Embolectomy Device," which is a 35 U.S.C. § 371 of PCT/IL09/00834, filed on Aug. 30, 2009, which claims the benefits of priority under 35 U.S.C. §§ 119-120 to U.S. Provisional Application 61/119,369, filed on Dec. 2, 2008, and to U.S. Provisional Application 61/093,173, filed on Aug. 29, 2008, the entire disclosures of which are incorporated herein by reference.

TECHNICAL FIELD

Embodiments of the present disclosure generally relate to devices and methods for treating occlusions within vasculature. More particularly, embodiments of the present disclosure relate to devices and methods for removal of clots (e.g., emboli and thrombi) found in blood vessels, among other things.

TECHNICAL BACKGROUND

Blood clots (e.g., emboli and thrombi) are examples of blockages that may form in mammalian blood vessels. A clot in an individual's blood vessel may become dangerous when it restricts blood flow, thereby placing the individual at risk for medical traumas, such as a stroke or a heart attack. Therefore, there may be a need to remove clots that are lodged within blood vessels.

A variety of devices and procedures have been used to remove clots from blood vessels. For example, a catheter with a balloon on its distal tip may be inserted into a blood vessel and passed through the clot, after which the balloon is inflated. The balloon may then be withdrawn from the blood vessel to remove the clot.

Another example of a clot removal device is a catheter containing a spiral section at its distal end. The catheter with spiral section may be delivered to a clot site within a blood vessel, and the spiral section may then be used to cut into the clot. The spiral section, therefore, may grasp to an inner portion of the clot prior to withdrawing the clot from the blood vessel.

One risk that exists with clot removal devices is that a piece of the clot may break away during the removal process, travel through the vasculature, and cause traumatic damage. This may occur for various reasons. For example, if the clot removal device passes through the clot prior to deployment, the pre-deployment activity can disrupt the clot, causing pieces to break away. Further, there is an increased risk of deploying a device in uninvolved distal territory.

SUMMARY

Embodiments of the present disclosure provide devices and methods for removing clots from blood vessels.

One embodiment consistent with the disclosure relates to a clot removal device, and includes a shaft and an elongate clot engagement element having one end connected to the shaft and a distal end remote from the end connected to the shaft, where the shaft and elongate clot engagement element having a principal longitudinal axis. Consistent with this disclosure, the distal end can include an end formation forming a curved contact surface at the distal end, and the end formation can be displaced to one side of the principal longitudinal axis.

In certain embodiments, the engagement element can include a coil, and/or the engagement element can be sized to be movable within a capture element upon removal of a sheath. In a further aspect, the engagement element can be sized to be rotatable within a capture element upon removal of a sheath.

In certain embodiments, the end formation can include a curved section of the engagement element. The curved section can have a J-shape. In another embodiment, the curved section or J-shape can have two curved portions, where the two curved portions are separated by a substantially straight portion.

In certain embodiments, the end formation can alternatively or additionally include an over-sized tip, such as a ball-like formation, at the distal end.

In another embodiment consistent with the disclosure, the embodiment relates to a method of removing a clot from a blood vessel. The method can include deploying a clot removal device into a blood vessel, where the clot removal device includes a shaft and an elongate clot engagement element having one end connected to the shaft and a distal end remote from the end connected to the shaft, and where the shaft and elongate clot engagement element have a principal longitudinal axis. The method can further include advancing the device in a blood vessel to a junction of multiple blood vessels, rotating the shaft and engagement element about the principal longitudinal axis such that the end portion faces a selected blood vessel, advancing the device along the selected blood vessel to engage a clot, and withdrawing the device from the blood vessel.

Additional aspects of the disclosure will be set forth in part in the description which follows, and in part will be readily ascertainable from the description, or can be learned by practice of the disclosure.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the disclosure and together with the description, serve to explain the principles of the disclosure.

BRIEF DESCRIPTION OF THE DRAWINGS

FIGS. 9-11, 12A, and 12B are views of an embodiment of an engagement element having an end formation.

FIGS. 13A-13D are sectional views of a body portion showing steps of a method of removing a clot from the body portion, using the medical device of FIG. 11.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to medical devices and methods for treating occlusions in a body. More particularly, embodiments of the present disclosure relate to devices and method for removing clots, including, but not limited to, emboli and thrombi from blood vessels. It should be emphasized, however, that embodiments of the present disclosure can also be utilized in other medical procedures where removal of a blockage or a foreign body is desired.

In accordance with embodiments of the disclosure, there may be provided a clot removal device including an expandable clot engagement element. An expandable clot engagement element can be any structure that, upon deployment in a blood vessel, can grip, grasp, circumscribe, or retain and/or retrieve a blood clot or other obstruction.

Figure 1A:
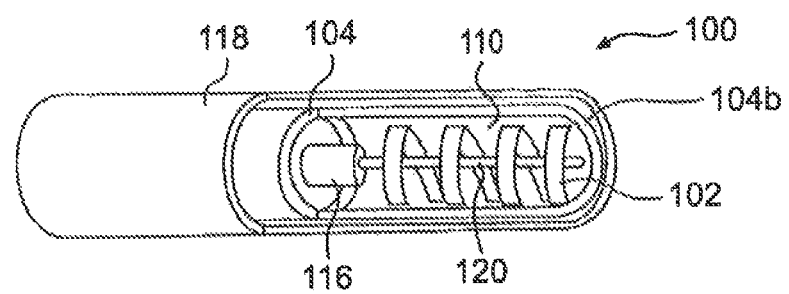
FIG. 1A is a sectional view of a medical device for removing a clot from a blood vessel, consistent with an embodiment of the disclosure.

FIG. 1A illustrates one example of a clot engagement element 102, in connection with exemplary clot removal device 100. For purposes of this disclosure, "proximal" refers to the end closer to the device operator during use, and "distal" refers to the end further from the device operator during use.

Figure 1B:
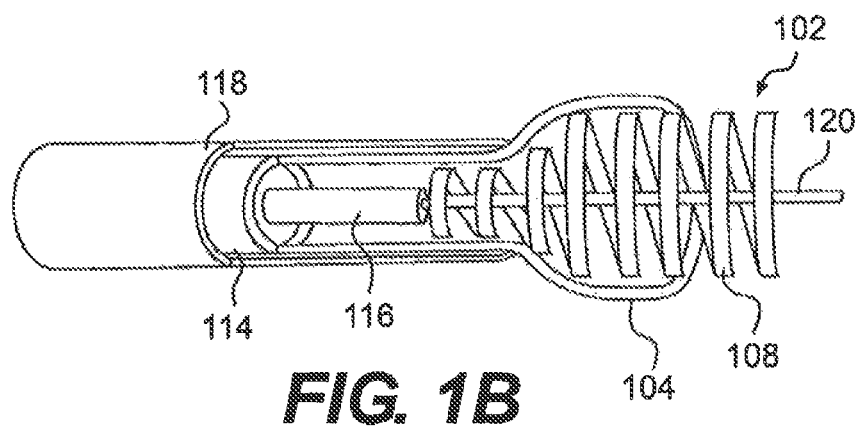
FIGS. 1B and 1C are a sectional views of a the medical device of FIG. 1A in expanded configurations.
Figure 7A:
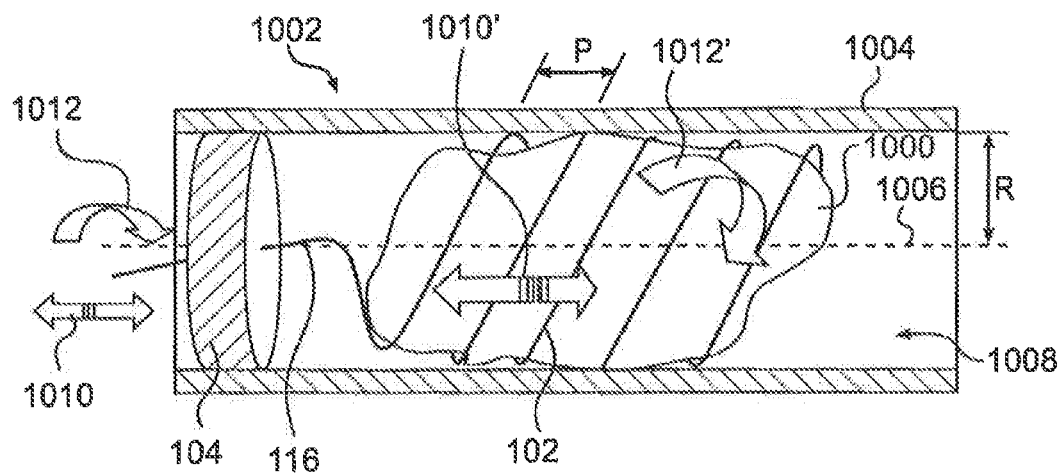
FIGS. 7A-7B are sectional views of the body portion of FIGS. 6A-6B showing movement of a clot engagement element during a method of removing a clot from the body portion, using the medical device of FIG. 1A.

As illustrated in FIG. 1B, in one embodiment, clot engagement element 102 can include a coil with one or more windings 108. The windings 108 can be angled relative to a longitudinal axis 1006 of a blood vessel 1002 (FIG. 7A). The angle of the windings 108 can range from approximately 0 degrees to approximately 180 degrees, and more preferably from approximately 90 degrees to approximately 180 degrees.

Figure 6A:
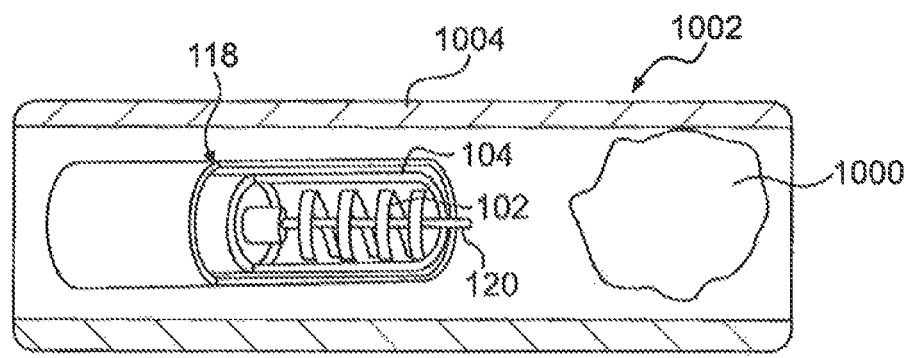
FIGS. 6A-6B are sectional views of a body portion showing steps of a method of removing a clot from the body portion, using the medical device of FIG. 1A.
Figure 6B:
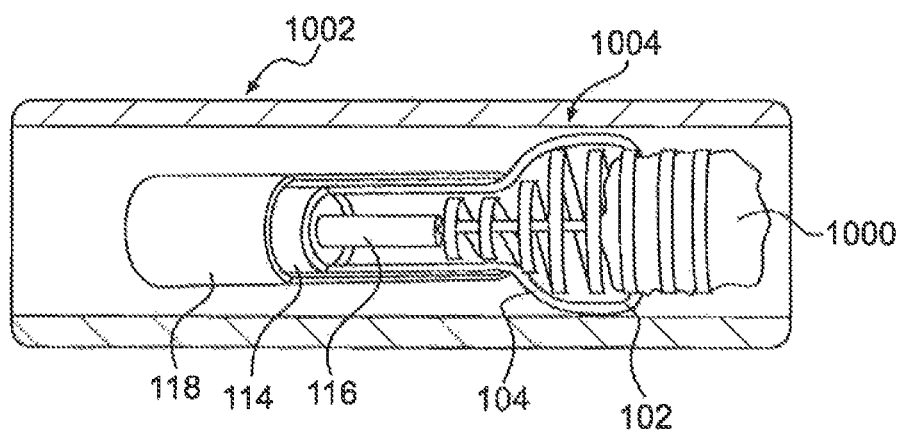

A plurality of windings 108 can further form a helical configuration, whereby the plurality of windings 108 share a substantially constant pitch P and/or a substantially constant radius R, as illustrated with reference lines in FIG. 7A. Thus, during rotation, adjacent windings having the same radius and pitch will follow substantially the same path of rotation. Alternatively, the one or more windings 108 can includes a varied pitch and/or a varied radius. The one or more windings 108 can be any shape and/or configuration such that they can be configured to rotate about a clot lodged within a blood vessel, to grasp at least a portion of the outer circumference of the clot, and to separate the clot from the blood vessel (FIG. 6B). For example, the one or more windings 108 can be wound in any suitable shape, including, but not limited to a circle and an oval. The one or more windings 108 can also be a continuous piece of material. The continuous piece of material can have any suitable cross-sectional shape, including, but not limited to, a circle, an oval, a polygon, or any other shape that is capable of being wound.

The one or more windings 108 can further include an atraumatic bottom, clot contacting surface that can be substantially flat or rounded. The bottom, clot contacting surface of the one or more windings 108 can mitigate the tendency of a clot 1000 to break into multiple pieces upon contact. Further, the bottom, clot contacting surface of the one or more windings 108 can be textured for enhanced gripping of a clot 1000. A top, exterior surface of the one or more windings 108 can also be an atraumatic surface. The atraumatic top, exterior surface of the one or more windings 108 can mitigate damage to tissue that the one or more windings 108 may contact at a clot site. Windings 108 can also include a coating on their top and/or bottom surfaces. The coating can include, but is not limited to, a lubricant and/or an anesthetic.

Clot engagement element 102 can further be a spring-like member configured to self-expand and retract. Expansion and retraction can be in longitudinal and/or radial directions. Accordingly, clot engagement element 102 can include a contracted configuration (FIG. 1A) and an expanded configuration (FIG. 1B). The contracted configuration can be maintained when a sheath 118 substantially surrounds an outer surface of clot engagement element 102. The expanded configuration can be achieved when sheath 118 is removed from at least a portion of the outer surface of clot engagement element 102 (Sheath 118 will be discussed in further detail below).

Clot engagement element 102 can be configured to expand to approximately an inner diameter of a blood vessel 1002 (FIG. 7A). Expansion to approximately an inner diameter of blood vessel 1002 can result (but not necessarily will result) in clot engagement element 102 exerting a force on a wall 1004 of blood vessel 1002. If a force is exerted on the vessel wall 1004, the force can result in separation of a clot 1000 from wall 1004 of blood vessel 1002. The resulting separation can be beneficial because in many instances, clot 1000 can be lodged in blood vessel 1002. Accordingly, separation of clot 1000 from wall 1004 of blood vessel can reduce the amount of force required to further remove clot 1000 from blood vessel 1002 and mitigate the tendency of clot 1000 to break into multiple fragments during removal from blood vessel 1002.

A shaft 116 can extend from a proximal end of clot engagement element 102. Shaft 116 can be an elongate member configured to control rotational and longitudinal movement of clot engagement element 102. For example, as illustrated in FIG. 7A, movement of shaft 116 in the directions shown by arrow 1010 can cause movement of clot engagement element 102 in the directions of arrow 1010'. Further, rotation of shaft 116 in the direction of arrow 1012 can cause rotational movement of clot engagement element 102 in the direction of arrow 1012'.

Shaft 116 can have any shape and/or configuration so long as shaft 116 can be configured to rotate and advance clot engaging element 102. Further, shaft 116 can have any suitable cross-sectional shape so long as shaft 116 can be configured to rotate. (FIG. 7A).

While the foregoing described embodiment presents an example of clot engagement element 102 as a wound structure, in a broader sense, the clot engagement element can have any shape and/or configuration so long as it is capable of grasping and removing a clot from a blood vessel. Further, the clot engagement element can be any size such that it is capable of traversing a lumen of a blood vessel.

The clot engagement element can be constructed of any suitable biocompatible material having sufficient flexibility and/or rigidity to traverse the lumen of the blood vessel. Biocompatible materials can include, but are not limited to, synthetic plastics, stainless steel, ePTFE, PTFE, metal-polymer composites, and metal alloys of nickel, titanium, nickel-titanium, copper cobalt, chromium, and iron.

In broader embodiments of the disclosure, a clot engagement element can include any structure or mechanism capable of engaging with a clot or other obstruction. For example, a clot engaging element can include one or more hooks, forceps, expandable cages, expandable balloons, or thermal or chemical mechanisms for causing a mechanical structure to connect with a clot or obstruction.

In accordance with at least some embodiments of the disclosure, there can be provided an expandable clot capture element. An expandable clot engagement element can be any structure that, upon deployment in a blood vessel, is able to capture a clot that has been engaged by a clot engaging element.

Consistent with an exemplary embodiment of the disclosure, an exemplary clot capture element 104 is illustrated in FIG. 1. The clot capture element 104 can be constructed to enable clot engagement element 102 to be movable therein upon deployment in a blood vessel. For example, upon removal of sheath 118 as will be described later in greater detail, clot engagement element 102 can be configured to rotate, expand, and/or longitudinally slide within clot capture element 104.

Figure 1C:
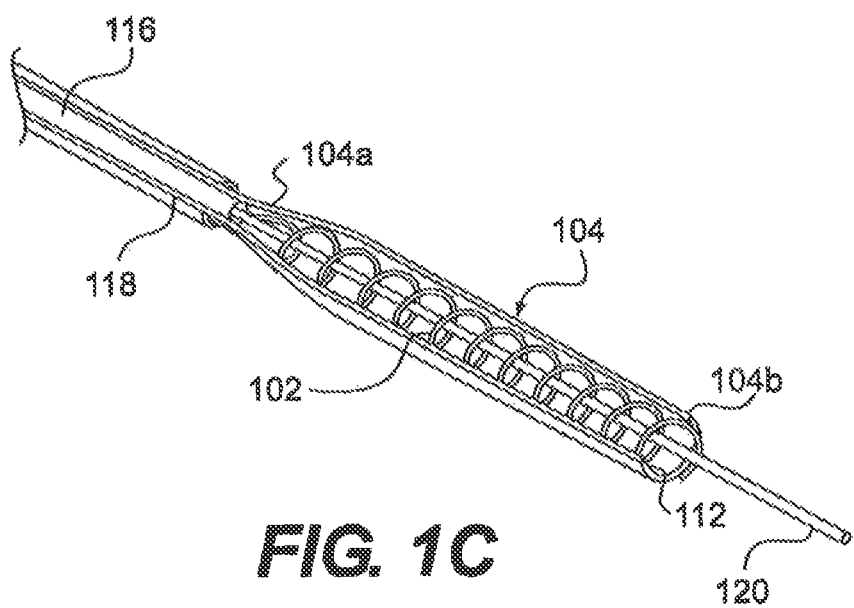

As illustrated in FIG. 1C, clot capture element 104 can include, but is not limited to, a catheter having a proximal end 104a and a distal end 104b. Proximal and distal ends 104a, 104b can each include an opening therein 112. Opening 112 at proximal and distal ends 104a, 104b can be in communication with a central lumen 110 in clot capture element 104 (FIG. 1A). Central lumen 110 in clot capture element 104 can allow for insertion of clot engagement element 102, as well as other components that can aid in a medical procedure, including, but not limited to, an optional guidewire 120, vacuum source, illumination and/or imaging devices, and tools for grasping a clot.

Clot capture element 104 can further be configured to expand and contract. Accordingly, clot capture element 104 can be configured to transition between a contracted configuration (FIG. 1A) and an expanded configuration (FIG. 1B), in a spring-like manner, in response to movement relative to a surrounding sheath 118. Similar to clot engagement element 102, clot capture element 104 can be configured to expand to a size that is substantially the same as an inner diameter of blood vessel 1002 at a clot site. The expansion of clot capture element 104 to the inner diameter of blood vessel 1002 and exerted force on blood vessel wall 1004 at the clot site can aid in separating a clot 1000 from a wall 1004 of blood vessel 1002. The separation can result in a reduction of the required force to remove clot 1000 from blood vessel 1002. The separation can also aid in mitigating the tendency of clot 1000 to break into multiple pieces during removal of clot 1000 from blood vessel 1002.

Figure 2:
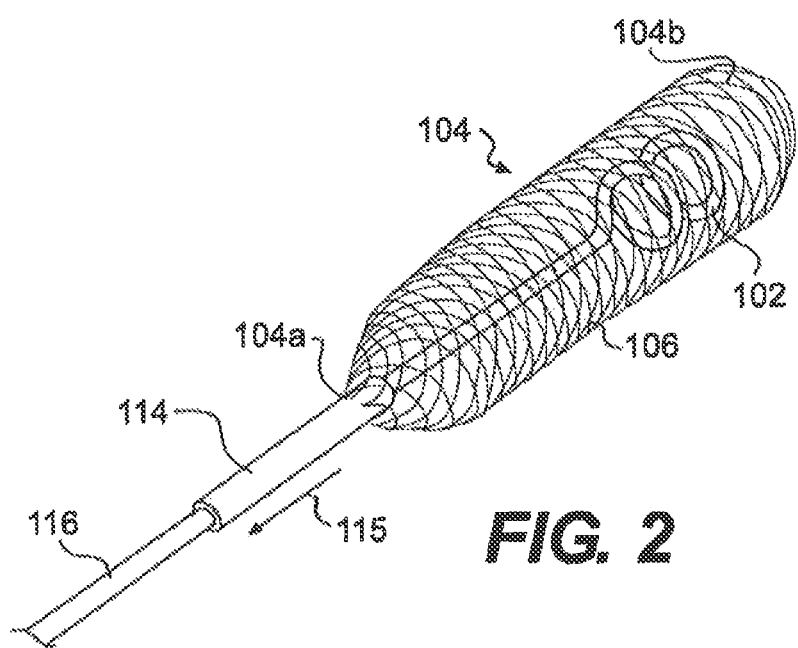
FIG. 2 is a perspective view of a clot capture element and clot engagement element of the medical device of FIG. 1A.
Figure 3A:
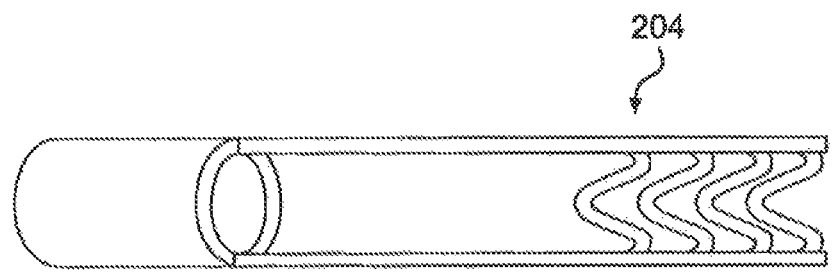
FIGS. 3A-3B are perspective views of a clot capture element, consistent with a further embodiment of the disclosure, in contracted and expanded configurations, respectively.
Figure 3B:
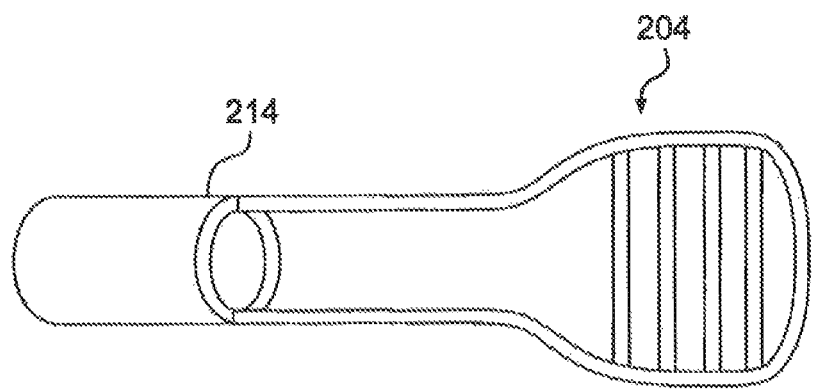

Clot capture element 104 can be any shape and/or configuration such that it can traverse a lumen of a blood vessel. In one embodiment, clot capture element 104 can be a hollow tube having a constant diameter. Alternatively, clot capture element 104 can have a diameter that varies along its length. For example, as illustrated in FIG. 2, clot capture element 104 can have a diameter that tapers at proximal end 104a, such that proximal end 104a can be configured to connect to a distal end of a control shaft 114 (Control shaft 114 will be discussed in further detail below).

Clot capture element 104 can be constructed of any known, suitable biocompatible material having sufficient flexibility and/or rigidity to traverse the lumen of the blood vessel. Biocompatible material of clot capture element 104 can further include properties that can enable clot capture element 104 to expand and contract in the manner previously discussed. Accordingly, biocompatible materials can include, but are not limited to, synthetic plastics, silicone elastomers, thermoplastic elastomers, nickel-titanium, stainless steel, ePTFE, PTFE, polyimides, polyamides, HDPE, polypropylene, polyvinylchloride, LDPE, metal-polymer composites, and metal alloys.

Clot capture element 104 can include a single biocompatible material or a combination of multiple biocompatible materials. In one embodiment, clot capture element 104 can include a variety of biocompatible materials, such that the type and properties of the biocompatible material can vary dependent on the location of the biocompatible material on clot capture element 104. For example, distal end 104b of clot capture element 104 can include materials having spring-like properties. Such biocompatible materials can include, but are not limited to, polyurethanes, low density polyethylene, polyvinylchloride, Nitinol and THV.

It may be desired to have proximal end 104a of clot capture element 104 include a stiffer biocompatible material than that of distal end 104b. The biocompatible material of proximal end 104a of clot capture element 104 can be any suitable degree of stiffness, so long as clot capture element 104 can be configured to traverse a lumen of a blood vessel. Accordingly, the biocompatible materials of proximal end 104a of clot capture element 104 can include, but are not limited to, polyimides, polyamides, high density polyethylene, polypropylene, polyvinylchloride, PTFE, polysulfones, copolymers and blends or mixtures of the aforementioned materials.

Clot capture element 104 can be a unitary structure, formed of a continuous piece of material. Alternatively, as illustrated in FIG. 2, clot capture element 104 can include multiple components 106. In one embodiment, for example, the multiple components 106 can include a plurality of woven braids intertwined to form a mesh-like structure (FIG. 2). The plurality of woven braids 106 can be connected to one another via any known means. Alternatively, the mesh-like structure can be in the form of a net, and the plurality of woven braids 106 can cross one another without being connected, whereby the plurality of woven braids 106 can be configured to move relative to one another. Additionally, the plurality of woven braids 106 can include a plurality of wires. The wires can be crossed and bent to form the mesh-like structure in a manner such that proximal and distal ends 104a, 104b of clot capture element 104 can be free of open ends of wires (FIG. 2). An absence of open ends can result in reduced trauma to the blood vessel. In other embodiments, free open ends can be used. In some of those embodiments, the open ends can be bent slightly inward or can be otherwise physically structure to minimize vessel trauma.

When a mesh-like structure is employed in the clot capture element 104, the mesh can be constructed in a manner similar to a Chinese finger trap, such that longitudinal retraction forces cause the cylindrical structure to contract radially.

Thus, regardless of other structure that can be employed, one embodiment of the disclosure can include a tubular clot capture element, wherein the clot capture element is configured for deployment in a blood vessel for surrounding a clot, the clot capture element having an opening therein configured to receive and guide a clot engaging element, the clot capture element being configured to radially contract upon retraction, such that when the clot capture element surrounds a clot and is retracted in a longitudinal direction of the blood vessel, the clot capture element is configured to exert a radially inward compression force on the clot.

Thus, for example, one embodiment of the disclosure can simply be the structure of capture element 104 in FIG. 2, which has a tubular shape formed of a mesh 106 with an opening 112 at proximal end 104*a* for receiving and guiding a shaft 116. As the result of its mesh-like structure, upon retraction, the capture element 104 contracts radially inward.

The mesh-like structure can be a net or it can be braided. The net itself can include a plurality of crossing braids such that the crossing braids are movable relative to each other. The net can include a plurality of wires where one or more of the proximal and distal ends of the capture element are free of open ends of wires (see, e.g., distal end of capture element 104 in FIG. 2, where the there are no exposed free ends of wires.).

Figure 4A:
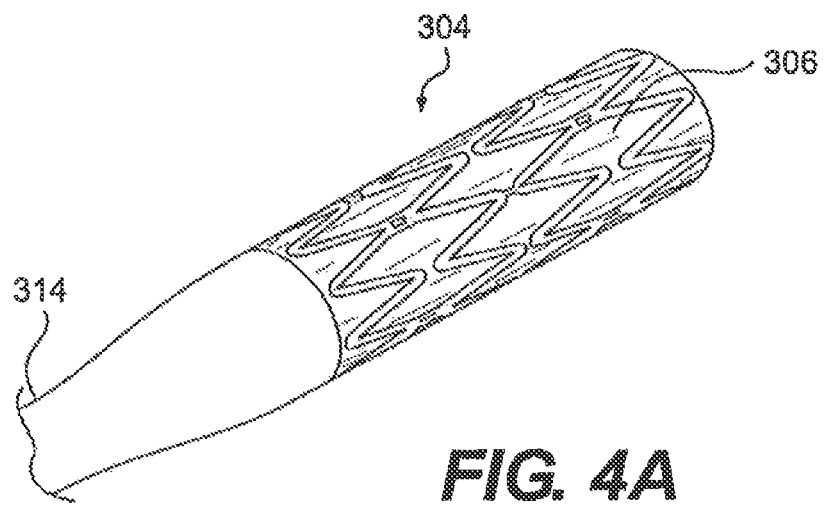
FIGS. 4A-4B are perspective views of a clot capture elements, consistent with additional embodiments of the disclosure.
Figure 4B:
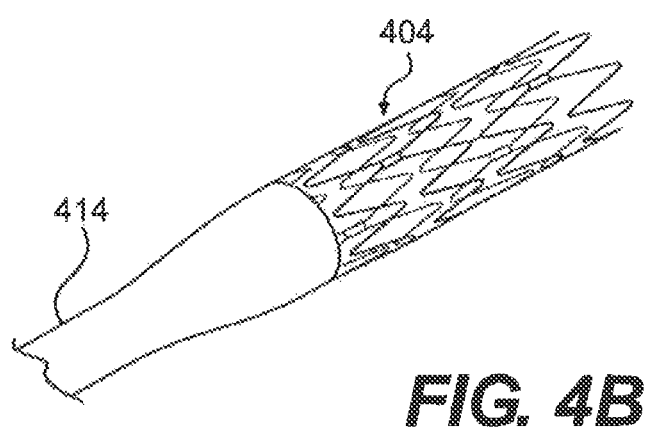

FIGS. 3A-3B and 4A-4B illustrate alternatives to the mesh-like structure, which can include any suitable self-expanding structure. For example, suitable self-expanding structures can include, but are not limited to, rounded coils, flat ribbon coils, a plurality of expandable rings (FIGS. 3A-3B), and/or stent-like structures (FIGS. 4A-4B). Self-expanding structures can further be supported between multiple layers of material 306 (e.g., polymers) which can provide suitable structure to clot capture element 104.

Clot capture element 104 can further include an atraumatic exterior surface that can limit tissue damage upon deployment at a clot site. Clot capture element 104 can also include a coating on its exterior and/or interior surfaces. The coating can include an anesthetic and/or a lubricant, which can aid in deployment of clot capture element 104 and clot engagement element 102 and/or can aid in movement of clot engagement element 102 within clot capture element 104.

As noted above, proximal end 104*a* of clot capture element 104 can be connected to control shaft 114. (See, e.g., FIG. 2) Control shaft 114 can be an elongate member configured to pull clot capture element 104 into the contracted configuration. Elongate member of control shaft 114 can be a hollow tube with a solid wall construction, a braided wall construction, a wound wall construction, a hypo-tube (i.e., solid wall construction with portions removed to facilitate flexing. The hollow tube can have openings on each end such that control shaft 114 can be in communication with central lumen 110 (FIG. 1) of clot capture element 104. Control shaft 114 can thereby allow for passage of tools, including, but not limited to a guidewire 120, and instrumentation for engaging with a clot 1000. Control shaft 114 can further allow for passage of shaft 116 of clot engagement element 102, as illustrated, for example in FIG. 2. Alternatively, control shaft 114 can be of solid construction, and shaft 116 can be positioned adjacent shaft 114, as opposed to running through it.

Shaft 116 can have a diameter that is less than a diameter of control shaft 114, which can allow for clot engagement element 102 to move along a longitudinal axis of clot capture element 104. Shaft 116 can also include a friction minimizing exterior surface. For example, the exterior surface of shaft 116 can be smooth and/or can include a lubricious coating such that shaft 116 can slide with relative ease within control shaft 114. Shaft 116 can further include a lumen therein. The lumen can be in communication with clot capture element 104. The lumen can also be in communication with a lumen 1008 in a blood vessel 1002 when clot removal device 100 is delivered to a clot site. Accordingly, the lumen can allow for insertion of tools useful during a clot removal procedure, including, but not limited to, a guide wire 120, a suction device, illumination devices, imaging devices, and/or suitable instrumentation for grasping a clot.

Control shaft 114 can include a diameter sized to receive shaft 116 in order to allow clot engagement element 102 to be moved within clot capture element 104 through movement of shaft 116. Shaft 116 can have a length that is longer than a length of control shaft 114 (FIG. 2) such that control shaft 114 can at least partially surround shaft 116, which can allow for a device operator to control longitudinal and rotational movement of clot engagement element 102. Control shaft 114 can further be configured to maintain a portion of shaft 116 of clot engagement element 102 in a non-contacting relationship with blood vessel wall 1004 and can be configured to maintain clot engagement element 102 in a desired position relative to clot 1000 at a clot site. Accordingly, control shaft 114 can act as a stabilizer for clot engagement element 102 when clot engagement element 102 is within clot capture element 104. For example, the diameter of control shaft 114 can be large enough to allow for longitudinal and rotational movement of shaft 116, but small enough to prevent shaft 116, and thereby clot engagement element 102, from substantially deviating from a predetermined location relative to clot 1000. Thus, one function of control shaft can be to center shaft 116 within the vessel, such that when engagement element 102 is rotated, the rotation occurs in a substantially longitudinal direction of the vessel.

In the absence of control shaft 114, or in addition to it, centering of the engagement element within the vessel can occur as the result of a tapering of capture element 104, or through the use of a spacer, not shown, for centering shaft 116 in the vessel. In this regard, another embodiment of the disclosure can include a clot removal device, having a shaft, a clot engagement element on an end of the shaft, the clot engagement element and the shaft being configured for deployment in a blood vessel; and a stabilizer configured to at least partially surround the shaft and to maintain a portion of the shaft in a non-contacting relationship with the blood vessel wall.

As depicted in FIG. 2, for example, shaft 116 can be maintained in non-contacting relationship with the vessel wall through control shaft 114's central interconnection to capture element 104. Thus, when shaft 116 enters the lumen defined by capture element 104, it can be biased in a direction toward the center of the vessel. This, in turn, can help to maintain the engagement element in a manner that, when rotated, it can tend to rotate in the longitudinal direction of the vessel rather than substantially transverse to the longitudinal direction. This is just one example of a stabilizer structure. Any structure that can hold an engaging element's shaft away from a vessel wall is also contemplated to be encompassed by this embodiment.

Control shaft 114 can also be configured to transition clot capture element 104 from the expanded configuration to an at least partially contracted configuration. For example, movement of control shaft 114 in the direction shown by arrow 115 in FIG. 2 can result in an applied force to proximal end 104a of clot engagement element 104. The applied force to proximal end 104a of clot capture element 104 can also be in the direction shown by arrow 115, which can thereby result in contraction of clot capture element 104.

Figure 7B:
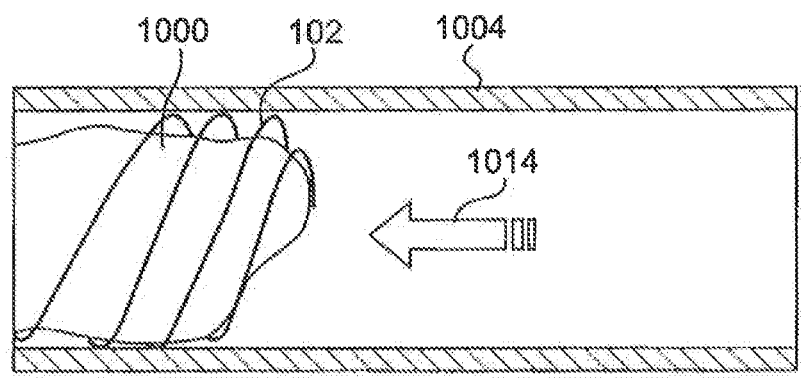
Figure 7C:
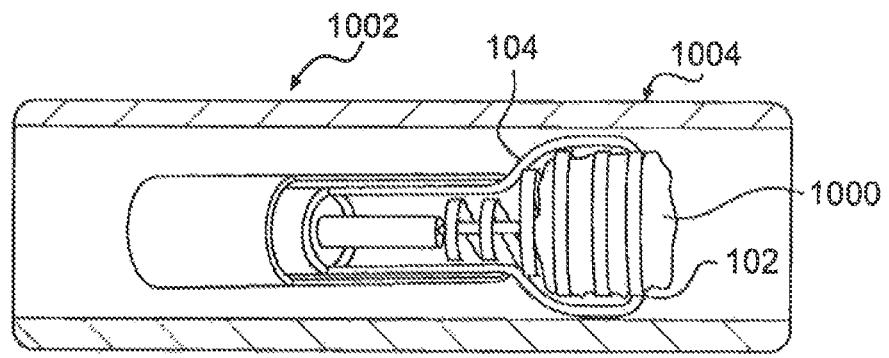
FIGS. 7C-7D are sectional views of the body portion of FIGS. 6A-6B showing steps of removing a clot from the body portion, using the medical device of FIG. 1A.
Figure 7D:
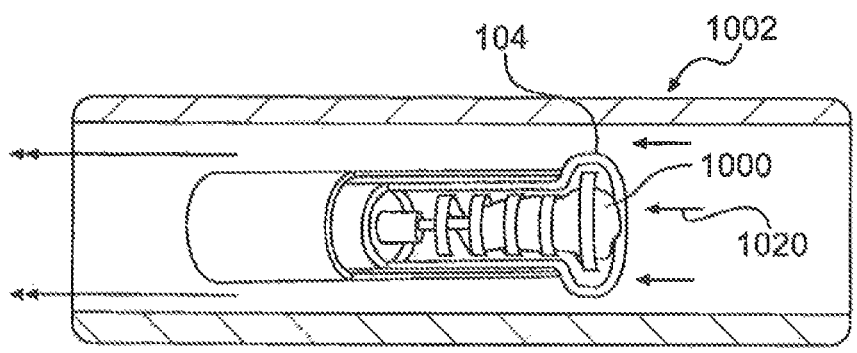
Figure 8:
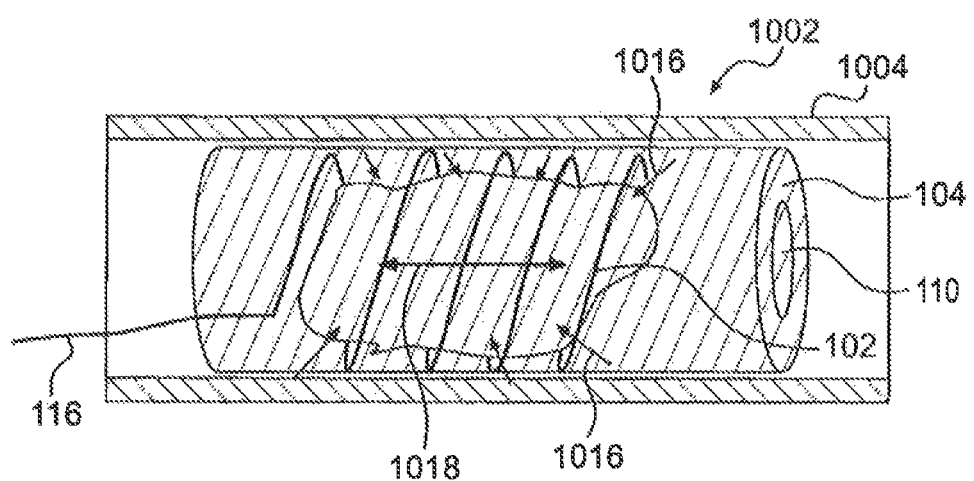
FIG. 8 is a sectional view of the body portion of FIGS. 6A-6B showing forces acting on a clot during a method of removing the clot from the body portion, using the medical device of FIG. 1A.
Figure 9:
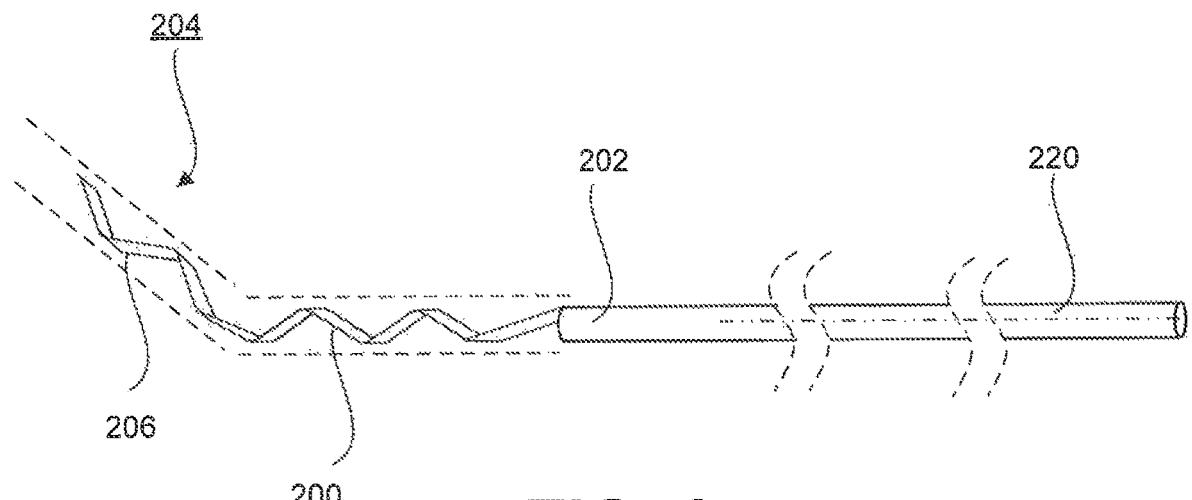

During retraction, clot capture element 104 can contract, exerting forces 1016, 1018 (FIG. 8) on clot 1000 and/or clot engagement element 102 when clot 1000 and/or clot engagement element 102 are within central lumen 110 of clot capture element. Forces 1016, 1018 can maintain clot 1000 within central lumen 110 of clot capture element 104 during removal of clot 1000 from a blood vessel 1002 and can mitigate a tendency of clot 1000 to break into multiple pieces. The clot can then be retrieved from the vessel with the clot retained solely within the capture element and engagement element, as illustrated in FIGS. 7A and 7B. Alternatively, for clots small enough to fit within sheath 118, the clot can be pulled into the sheath 118 before removal from the vessel, as illustrated in FIGS. 7C and 7D. In this manner, the sheath 118 can exert further holding forces on the clot.

In accordance with at least some embodiments, a sheath can be provided, surrounding and compressing the capture element and the engagement element. The sheath can be removable to thereby enable the capture element to expand in a blood vessel in which the sheath is deployed, and to enable the engagement element to expand within the capture element. A sheath can be any structure that is capable of retaining one or more of a clot engaging element and a clot capture element, while being capable of sufficiently flexing in order to deploy one or more of those elements in a vessel.

Consistent with at least some exemplary embodiments of the disclosure, an exemplary sheath 118 is illustrated in FIG. 1. Clot engagement element 102 and clot capture element 104 can be delivered to a clot site within the sheath 118. Sheath 118 can be a hollow tubular structure having a central lumen configured to surround clot engagement element 102 and clot capture element 104 (FIG. 1A). Sheath 118 can further be configured to protect clot engagement element 102 and clot capture element 104 as they follow a delivery path to the clot site. Accordingly, sheath 118 can be made of any suitable biocompatible material and have any suitable shape and/or configuration so long as sheath 118 can be configured to traverse a patient's vasculature while maintaining clot engagement element 102 and clot capture element 104 in their respective contracted configurations upon delivery to and removal from a clot site. Further, upon removal of clot engagement element 102 and clot capture element 104 from the clot site, the sheath can be configured to maintain a clot within its central lumen as well (FIG. 7D).

Additionally, sheath 118 can be configured to allow for controlled expansion of clot capture element 104 and clot engagement element 102. For example, as previously discussed, clot capture element 104 and clot engagement element 102 can be configured to expand upon removal of sheath 118. Sheath 118 can be retracted in a direction away from distal end 104b of clot capture element 104. Accordingly, sheath 118 can be removed at a rate that can control the rate of expansion of clot capture element 104 and clot engagement. Further, sheath 118 can be retracted a distance that can control the amount of clot capture element 104 and clot engagement element 102 that can be exposed and expanded (FIG. 1B). Alternatively, the sheath 118 can be substantially stationary, and the clot capture element 104 and clot engagement element 102 can be advanced, resulting in expansion of those elements.

In accordance with another embodiment of the disclosure there can be provided a tubular clot capture element having a first internal diameter, and a clot engaging element having a second external diameter, wherein the first diameter and the second diameter are selected to permit the clot engaging element to be rotated within the tubular clot capture element.

By way of example only, and as illustrated in FIG. 2 as well as the other figures, the inner diameter of clot capture element 104 can be sufficiently sized so that clot engaging element 102 is able to be rotated therein. Depending on the ultimate commercial design, this can provide the operator with the freedom to encircle a clot with an engaging element 102 at the same time that the clot is being drawn into the capture element 104. Or it can provide the operator with the ability to turn the clot once it is within the capture element 104. As such, the elements 102, 104 can be sized such that an outer surface area of the clot engaging element 102 can contact an inner surface area of the clot capture element 104.

Figure 5:
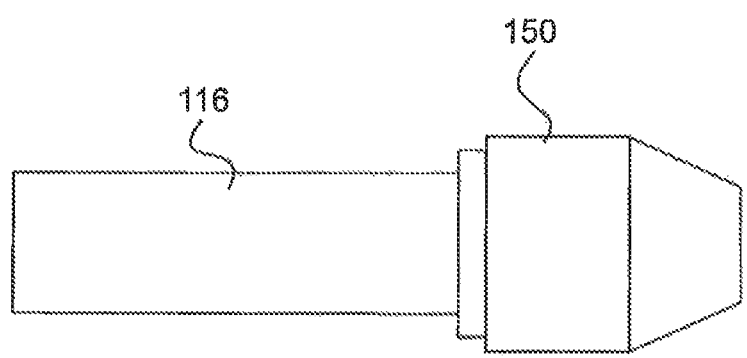
FIG. 5 is a perspective view of a conventional locking mechanism for use with the medical device of FIG. 1A.

During operation of clot removal device 100, a device operator may find it useful to prevent movement of clot engagement element 102 relative to clot capture element 104. This can be desirable, for example, during delivery of clot removal device 100 to the clot site and/or during removal of clot 1000 from a patient. Accordingly, FIG. 5 illustrates a locking mechanism 150 that can be used with clot removal device 100 for selectively locking shaft 116 of clot engagement element 102 in a fixed position with respect to control shaft 114 of clot capture element 104. When locking mechanism 150 is rotated in one direction locking can occur, and when rotated in an opposite direction, release can occur. Locking mechanism can be any suitable device that selectively prevents relative movement between the clot engagement element and the clot capture element. Examples of locking mechanisms can include, but are not limited to, snap locks, rotational locks, and interference fits. For example, in one embodiment, locking mechanism can be a torquer 150. A similar or differing locking mechanism can be used to control relative movement between sheath 118 and capture element 104.

Clot removal device 100 can also include a component that can allow a device operator to know the location of clot removal device 100 as it travels to the clot site. Location components can include, but are not limited to, radiopaque markers, sensors, and/or imaging devices. In one embodiment, for example, distal end 104b of clot capture element 104 can include a radiopaque marker (not shown).

Turning now to FIGS. 6A-6B, 7A-7D, and 8, a procedure of removing a clot from a blood vessel is illustrated using clot removal device 100 shown in FIG. 1A. Clot removal device 100 can be delivered to a clot site within a blood vessel 1002. Delivery of clot removal device 100 can include transporting sheath 118, which can substantially surround clot engagement element 102 and clot capture element 104, within a patient's vasculature to a location proximate a clot 1000. A device operator may insert clot removal device 100 over a guidewire 120 in order to assure clot removal device 100 follows a correct path to the clot site. During delivery within sheath 118, clot engagement element 102 can be substantially surrounded by clot capture element 104, as illustrated in FIG. 1A. Alternatively, clot engagement element 102 can be located outside of clot capture element 104, and can be pulled into clot capture element 102 after grasping clot 1000 during a later point in the procedure.

As previously discussed, a device operator may monitor the location of clot removal device 100 as it approaches the clot site via sensors, radiopaque markers, and/or imaging devices. Once clot removal device 100 has reached the clot site, the device operator may remove guidewire 120 from clot removal device 100. The device operator may retract the sheath 118 (or advance the engagement element) sufficiently so that the engagement element 102 can rotate. Alternatively, the sheath 118 may be removed in its entirety. Upon diassociation of the sheath 118 from clot engagement element 102, clot engagement element 102 can then expand radially and be movable (e.g., longitudinal and rotational movement) within clot capture element 104. Both the clot engaging element 102 and the clot capture element 104 can be self-expanding in a spring-like manner. Clot capture element 104 can expand to the approximate size of the inner diameter of blood vessel 1002. As previously discussed, the expansion of clot capture element 104 can initiate separation of clot 1000 from blood vessel wall 1004.

The device operator may move shaft 116 of clot engagement element 102 in the direction of arrow 1010 towards clot 1000 and rotate shaft 116 in the direction of arrow 1012 which can cause clot engagement element 102 to engage with clot 1000. Longitudinal movement of shaft 116 can cause longitudinal movement of clot engagement element 102 in the direction of arrow 1010', and rotational movement of shaft 116 can cause rotational movement of clot engagement element 102 in the direction of arrow 1012'. Clot engagement element 102 may be moved along a longitudinal axis 1006 of blood vessel towards clot 1000. Upon a distal-most end of clot engaging element 102 reaching clot 1000, simultaneous longitudinal a rotational movement of shaft 116 can cause clot engagement element 102 to encircle clot 1000. If windings 108 of clot capture element 102 have a substantially constant pitch and a substantially constant radius, then as the capture element 102 is wound, the windings can follow a single path, minimizing trauma to the clot, and thereby minimizing risk that the clot will break apart. As clot engagement element 102 encircles clot 1000, clot engagement element 102 can be between clot 1000 and clot capture element. In some instances of use, rotation of clot engagement element 102 can result in an Archimedes screw effect, drawing the clot further into the engagement element 102 without the need to significantly advance the engagement element. The extent of the Archimedes effect, and whether it occurs at all, can vary depending on the specific nature of the clot and the extent of its connection to the vessel wall 1004.

Encircling of clot 1000 by clot engagement element 102 can cause additional expansion of clot engagement element 102. As previously discussed, radial expansion of clot engagement element 102 can cause an outer surface of clot engagement element 102 to exert a force on a wall 1004 of blood vessel 1002, which can further aid in separating clot 1000 from blood vessel wall 1004. The separation can aid in reducing the force needed to remove clot 1000 from blood vessel 1002. The separation can also aid in mitigating the tendency of clot 1000 to break into multiple pieces during removal of the clot from blood vessel 1002.

The device operator may encircle clot 1000 with clot engagement device such that the device operator is capable of pulling clot engagement element 102 and clot 1000, together, into clot capture element 104. Accordingly, the device operator may move shaft 116 in the direction of arrow 1014 such that clot 1000 encircled by clot engagement element 102 can be pulled through opening 112 and into central lumen 110 of clot capture element 104.

As the device operator pulls clot 1000 and clot engagement element 102 into central lumen 110 of clot capture element 104 in the direction of arrow 1014, the device operator may also pull control shaft 114 of clot capture element 104 in the direction of arrow 115. This pulling can result in clot capture element 104 applying radially contracting forces 1016 and a longitudinal shearing force 1018 to clot 1000 and clot engagement element 102. These applied forces can aid the device operator in maintaining clot 1000 within clot capture element 104 and removing clot 1000 from blood vessel 1002 without breaking clot 1000 into multiple pieces. And if the clot does break, capture element 104 can protect against pieces becoming loose in the bloodstream.

As illustrated in FIG. 7D, the simultaneous pulling of clot capture element 104 and clot 1000 encircled by clot engagement element 102 can result in the aforementioned components being drawn back into sheath 118 in the direction of arrow 1020. The drawing of clot engagement element 102 and clot capture element 104 back into sheath 118, can result in the transition of clot engagement element 102 and clot capture element 104 from the expanded configuration (FIG. 7C) to the contracted configuration (FIG. 7D). The device operator may then remove clot removal device 100 from the patient's vasculature along longitudinal axis 1006 of blood vessel 1002.

Alternatively, the clot can be removed from the vasculature without pulling the capture element and the engaging element back into the sheath. Instead, as the clot can be trapped within the capture element, the radial forces exerted upon retraction can be sufficient to compress the clot within the capture element such that the structure can be retracted in a substantially expanded form.

The device operator may alter the method of removing clot 1000 from blood vessel 1002 as necessary. For example, prior to positioning clot engagement element 102 for encircling of clot 1000, the device operator may insert instrumentation through central lumen of clot capture element 104 which can be necessary for cleaning out the clot site. Additionally, removal of clot 1000 can be accompanied by suitable tools for grasping and/or maintaining clot 1000 within clot capture element 104. For example, the device operator may employ a suctioning device at a proximal end of clot removal device 100. The suctioning device can further aid in pulling clot 1000 into clot capture element 104 and retaining clot 104 within clot capture element 104 as clot 1000 is drawn out of the patient's vasculature.

In accordance with another embodiment of the disclosure, a method of removing a clot from a blood vessel can include deploying a tubular clot capture element in a blood vessel, the clot capture element having an opening therein that receives and guides a clot engaging element, surrounding a clot with the clot capture element, and retracting the clot capture element in a longitudinal direction of the blood vessel, such that the clot capture element radially contracts, exerting a radially inward compression force on the clot. This embodiment of the disclosure can be practiced with any of the clot capture elements described above, including, clot capture element 104.

In accordance with yet another embodiment of the disclosure, a method of removing a clot from a blood vessel can include delivering a tubular clot capture element having a first diameter to a clot site and delivering a clot engaging element having a second external diameter to the clot site, wherein the first diameter and the second diameter are selected to such that the clot engaging element rotates within the tubular clot capture element. As described earlier in connection with FIG. 2, such a method can be accomplished, for example, when clot capture element 104 is delivered to a clot site, clot engaging element 102 is delivered to a clot site, and when the two elements' diameters permit the engaging element to be rotated within the capture element.

While the capture element and the engaging element can be deployed together, such as in the same sheath, the disclosure in its broadest sense does not necessarily so require. The engaging element can, for example, be delivered first, and the capture element can be subsequently delivered. Moreover, the engaging element when rotated can be sized to contact the inner wall of the capture element, or the engaging element can be sized to avoid contact.

In accordance with a further embodiment of the disclosure, a method for removing a clot from a blood vessel can include deploying a clot engagement element in a blood vessel, the clot engagement element can be located on an end of a shaft; and at least partially surrounding the shaft with a stabilizer to maintain a portion of the shaft in a non-contacting relationship with the blood vessel wall. This method can be practiced with or without a clot capture element, such as structure 104, and without regard to any specific stabilizing structure. As was previously noted, depending on design choice, some embodiments of the disclosure can benefit from a rotation of the engagement element 102 when the engagement element 102 is centered in the vessel. This can minimize the pressure exerted on the vessel walls, while maximizing movement of the engagement element 102 in the longitudinal direction of the vessel to surround the clot. By stabilizing, toward the center of the vessel, the shaft (e.g., shaft 116) that rotates the engagement element (e.g., 102), longitudinal motion can be maximized. Thus, stabilization can occur by surrounding shaft 116 with any structure that generally maintains it near the center of the vessel at locations proximate the intersection of shaft 116 and windings 108.

Figure 10:
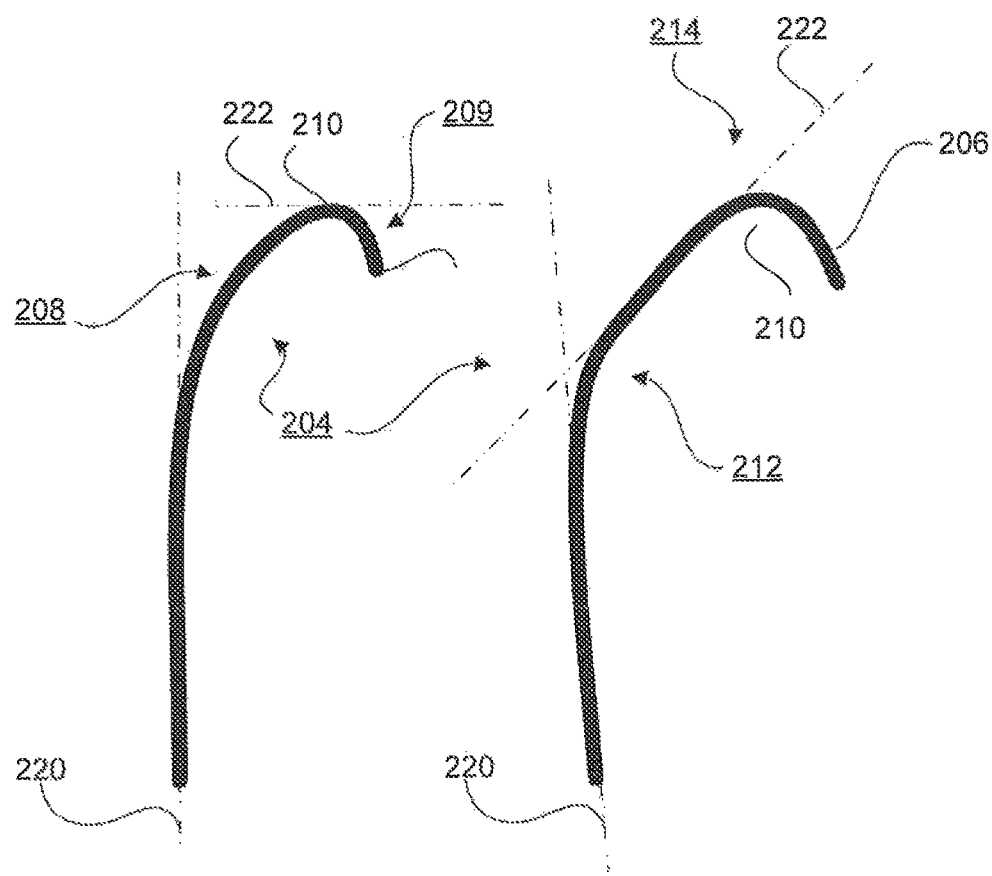
Figure 11:
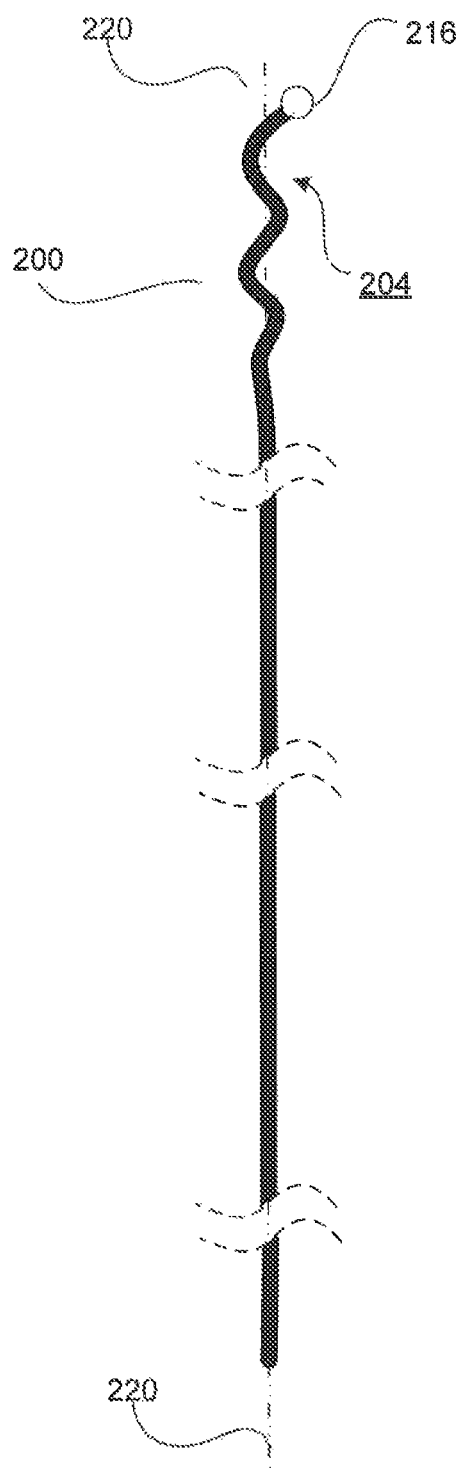

FIGS. 9-12 show further embodiments. It has been observed that clots have a tendency to become trapped at vessel bifurcations (junctions). The diameters of the blood vessels after a junction can be smaller than that of the parent vessel before the junction with the result that clots can be confined to these locations. In the embodiments of FIGS. 9-12, an engagement element in the form of a coil 200 is connected to a shaft 202. The coil 200 can be substantially similar to that described in relation to the embodiments described above. In the embodiments shown here, the distal end 204 of the coil 200 can have an end formation 206 that is displaced to one side of the principal axis 220 of the shaft 202 and coil 200. FIG. 10 shows two embodiments of an end formation 206 formed from at least two curves (208 and 209) in the distal end 204 of the coil 200, where each of the two curves 208 and 209 exhibit an overall angular deviation between 0-degrees and less than or equal to 90-degrees. In one embodiment, the distal end 204 exhibits first curve 208 (from principal axis 220) and second curve 209 (from second axis 222). The effect of this is that the extreme terminal point of the coil exhibits an angular deviation that is between 90-degrees and 180-degrees relative to the principal axis 220, and the leading part 210 of the coil, i.e. the part that will contact the walls of the blood vessels as the device is advanced to a clot, is curved and less likely to cause damage to the blood vessel. In the other embodiment of FIG. 10, the distal end 204 has two curves 212, 214 that are separated by a substantially straight portion. That is, there is a first curve 212 from principal axis 220 and a second curve 214 from second axis 222, and between the two portions is a substantially straight portion. Other curved forms and combinations of curves can also be used. In the embodiment of FIG. 11, the distal end 204 is provided with an over-sized end portion 216, in the form of a ball-like formation, which lies to one side of the coil 200. Although the coil in this embodiment is not curved (i.e., there is no overall deviation from the principal axis 220), the over-sized end portion 216 can also be used with a curved distal end 204 such as that shown in FIG. 9. The over-sized end 216 can be coated with a friction reducing material such as PTFE. The embodiments of FIGS. 12A and 12B are similar to the embodiment of FIG. 11, with the exception that the distal end 244 can includes a pronounced variation in pitch P and/in radius of the coil proximal to the over-sized end portion 216.

By displacing the distal end 204 and the distal end 244 from the principal longitudinal axis 220, an asymmetry is introduced into the system configuration that can be used to steer the device as it is advanced through a blood vessel. By rotating the device about the principal axis, the distal end can be placed in a desired direction such that advancing the device further causes the device to be deflected in the desired direction. For example, when the device reaches a junction in the blood vessel, rotating the device allows the distal end to be pointed towards the desired blood vessel branch. Advancing the device further causes the distal end to enter the desired vessel and the device can be further advanced to contact the clot. Other aspects of the device, such as the configuration of the clot capture element, can be as described above.

In further embodiments, a coil 400 with an angled tip 403, and a procedure for removing the clot 1000 from the blood vessel 1002 using the coil 400 is shown in FIGS. 13A-13D. As shown in these figures, a catheter 500 can be delivered to a clot site within a blood vessel 1002. Delivery of the catheter 500 can include inserting the catheter 500 within a patient's vasculature to a location proximate the clot 1000. In some embodiment, the coil 400 can be positioned within a lumen (not shown) of the catheter 500 during delivery of the catheter 500 to the clot 1000. In other embodiments, the coil 400 can be inserted into the lumen of the catheter 500 after the catheter 500 has been positioned proximate the clot 1000.

After delivery of the catheter 500 to a location proximate the clot site, the device operator can deploy the coil 400 from the catheter 500 into the vessel 1002. The angled tip 403 of the coil 400 can be rotated about a principal axis (as indicated by the arrow in FIG. 13B) so that the angled tip 403 (at a distal end of the coil 400) can be oriented in a desired direction. As discussed above, the coil 400 with the angled tip 403 can be configured such that advancing the coil 400 further along the vessel 1002 can cause the angled tip 403 of the coil 400 to be deflected in a desired direction. For example, when the device reaches a junction in the blood vessel 1002, the coil 400 can be rotated to allow the angled tip 403 to be oriented towards the desired blood vessel branch. Further advancement of the coil 400 can cause the angled tip 403 of the coil 400 to contact the clot 1000.

In addition to the use of the coil 400, the device operator can employ a suctioning device at a proximal end of the catheter 500 to apply suction to the distal end of the catheter 500. The suctioning device can be, for example, a pump or syringe coupled to the proximal end of the catheter 500. Suction can be applied intermittently before or after the procedure or throughout the duration of the procedure to maintain the integrity of the clot 1000 and to assist the operator to draw the clot 1000 back into the catheter 500.

In certain embodiments, suction can be applied prior to the deployment of the coil 400. In those embodiments, suction can be applied to pull the clot 1000 into the catheter 500. The coil 400 can then be deployed within the catheter 500 to contact the clot 1000 and retain the clot 1000 within the catheter 500 as the catheter 500 is withdrawn from the patient's vasculature.

Other embodiments of the disclosure will be apparent to those skilled in the art from consideration of the specification and practice of the invention disclosed herein. It is intended that the specification and examples be considered as exemplary only, with a true scope being indicated by the following claims.

What is claimed is:

1. A clot removal device configured for deployment from a proximal side of a clot location, the clot removal device comprising:
   a shaft having a proximal end and a distal end opposite from the proximal end, wherein a principal longitudinal axis extends between the proximal and distal ends of the shaft;
   a radially-expandable clot capture element;
   a sheath configured to surround the clot capture element; and
   a radially-expandable elongate clot engagement element configured to be surrounded by the clot capture element,
      wherein the elongate clot engagement element is configured for deployment to the clot location from the proximal side of the clot location, the elongate clot engagement element having a first end connected to the shaft and a second end opposite from the first end, and
      wherein the elongate clot engagement element is configured to engage a clot at the clot location by grasping a periphery of the clot with the second end of the elongate clot engagement element while avoiding a central region of the clot,
   wherein axial movement of the sheath relative to the clot capture element and the elongate clot engagement element controls the radial expansion of the clot capture element and the radial expansion of the elongate clot engagement element,
   wherein the elongate clot engagement element is helically coiled between the first end and the second end of the elongate clot engagement element, the second end of the elongate clot engagement element forming an opening configured to encircle the clot from the proximal side of the clot location, wherein the elongate clot engagement element is configured to define a substantially unobstructed channel on the clot removal device for encircling the clot from the proximal side of the clot location, and
   wherein a distal end of the elongate clot engagement element comprises an end formation configured to form a leading curved contact surface, the end formation being biased to deviate away from the principal longitudinal axis, wherein the end formation comprises a first bendable portion and a second bendable portion of the elongate clot engagement element, the first and second bendable portions each being biased to exhibit an angular deviation relative to the principal longitudinal axis such that the first bendable portion of the elongate clot engagement element is configured to be situated in a proximal direction from the second bendable portion.

2. The clot removal device of claim 1, wherein the first bendable portion and the second bendable portion of the elongate clot engagement element are separated by a straight portion of the elongate clot engagement element that is biased in a straightened configuration.

3. The clot removal device of claim 1, wherein the clot capture element is configured to:
   receive the elongate clot engagement element in a radially-expanded configuration and the clot encircled by the substantially unobstructed channel within the clot capture element when the clot capture element is in a radially-expanded configuration, and
   be pulled at least partially into the sheath while the clot capture element retains the elongate clot engagement element and the clot.

4. The clot removal device of claim 1, wherein the leading curved contact surface is configured to form the distal-most portion of the clot removal device.

5. The clot removal device of claim 1, wherein at least one of the clot capture element or the elongate clot engagement element are self-expandable such that the clot capture element and the elongate clot engagement element radially expand when the clot capture element and the elongate clot engagement element are removed from the sheath.

6. The clot removal device of claim 1, wherein at least a portion of the elongate clot engagement element is biased in an undulating configuration along the principal longitudinal axis.

7. The clot removal device of claim 1, wherein the second end of the elongate clot engagement element is biased to exhibit an angular deviation greater than 90° relative to the principal longitudinal axis.

8. A clot removal device configured for deployment from a proximal side of a clot location, the clot removal device comprising:
   a shaft having a proximal end and a distal end opposite from the proximal end, wherein a principal longitudinal axis extends between the proximal and distal ends of the shaft;
   a radially-expandable clot capture element;
   a sheath configured to surround the clot capture element; and
   a radially-expandable elongate clot engagement element configured to be surrounded by the clot capture element,
      wherein the elongate clot engagement element is configured for deployment to the clot location from the proximal side of the clot location, the elongate clot engagement element having a first end connected to the shaft and a second end opposite from the first end, and
      wherein the elongate clot engagement element is configured to engage a clot at the clot location by grasping a periphery of the clot with the second end of the elongate clot engagement element while avoiding a central region of the clot,
   wherein axial movement of the sheath relative to the clot capture element and the elongate clot engagement element controls the radial expansion of the clot capture element and the radial expansion of the elongate clot engagement element,
   wherein the elongate clot engagement element is helically coiled between the first end and second end of the elongate clot engagement element, the second end of the elongate clot engagement element forming an opening configured to encircle the clot from the proximal side of the clot location, wherein the elongate clot engagement element is configured to define a substantially unobstructed channel on the clot removal device for encircling the clot from the proximal side of the clot location at least when the elongate clot engagement element is in a radially-expanded configuration, wherein a distal end of the elongate clot engagement element comprises an end formation configured to form a leading curved contact surface, the end formation being biased to deviate away from the principal longitudinal axis such that the end formation is configured to steer the clot removal device to advance through a body lumen extending away from the principal longitudinal axis, and wherein the clot capture element is configured to receive the elongate clot engagement element and the clot encircled by the substantially unobstructed channel within the clot capture element when the clot capture element is in a radially-expanded configuration.

9. The clot removal device of claim 8, wherein a tip of the end formation comprises a ball-like formation.

10. The clot removal device of claim 8, wherein a portion of the helically coiled elongate clot engagement element that is proximal to a tip of the end formation exhibits a substantial variation in pitch.

11. The clot removal device of claim 8, wherein a portion of the helically coiled elongate clot engagement element that is proximal to a tip of the end formation exhibits a substantial variation in helix circumference radius.

12. The clot removal device of claim 8, wherein the clot capture element is configured to:
receive the elongate clot engagement element in the radially-expanded configuration and the clot encircled by the substantially unobstructed channel within the clot capture element when the clot capture element is in the radially-expanded configuration, and
be pulled at least partially into the sheath while the clot capture element retains the elongate clot engagement element and the clot.

13. The clot removal device of claim 8, wherein at least one of the clot capture element or the elongate clot engagement element are self-expandable such that the clot capture element and the elongate clot engagement element radially expand when the clot capture element and the elongate clot engagement element are removed from the sheath.

14. The clot removal device of claim 8, wherein at least a portion of the elongate clot engagement element is biased in an undulating configuration along the principal longitudinal axis.

15. The clot removal device of claim 8, wherein the end formation comprises:
a first bendable portion biased to exhibit angular deviation relative to the principal longitudinal axis;
a second bendable portion biased to exhibit angular deviation relative to the principal longitudinal axis; and
a straight portion situated between the first and second bendable portions, the straight portion being biased in a straightened configuration.

16. The clot removal device of claim 15, wherein the first bendable portion and the second bendable portion are biased to exhibit a total angular deviation greater than 90° relative to the principal longitudinal axis.

17. A method of removing a clot from a blood vessel, the method comprising:
deploying a clot removal device into the blood vessel on a proximal side of a clot location, wherein the clot removal device comprises:
a shaft;
a clot capture element;
a sheath surrounding the clot capture element; and
an elongate clot engagement element surrounded by the clot capture element,
wherein the elongate clot engagement element is configured for deployment to the clot location from the proximal side of the clot location, the elongate clot engagement element having one end connected to the shaft and a distal end remote from the end connected to the shaft, and
wherein the elongate clot engagement element is configured to avoid a central region of the clot and to engage the clot about a periphery of the clot,
wherein the shaft and the elongate clot engagement element have a principal longitudinal axis,
wherein the clot capture element and the elongate clot engagement element are expandable, the sheath being configured to control a rate of expansion of the clot capture element and the elongate clot engagement element, wherein the sheath is retractable, in a direction away from the distal end of the elongate clot engagement element, at a rate that controls the expansion rate of the clot capture element and the elongate clot engagement element,
wherein the elongate clot engagement element extends along a curved path defining a helix, and wherein the curved path defining the helix has an open end on a distal side thereof configured to encircle the clot from the proximal side of the clot location, with the distal end of the elongate clot engagement element being located substantially at the open end of the curved path defining the helix to define a substantially unobstructed channel on the clot removal device for encircling the clot from the proximal side of the clot location, and
wherein the distal end of the elongate clot engagement element comprises an end formation forming a leading curved contact surface, the end formation being displaced to one side of the principal longitudinal axis and the end formation being displaced to one side of the substantially unobstructed channel for encircling the clot from the proximal side of the clot location, wherein the end formation comprises a curved section of the elongate clot engagement element, the curved section comprising first and second curves of the elongate clot engagement element, the first and second curves each exhibiting an angular deviation relative to the principal longitudinal axis;
advancing the clot removal device in the blood vessel to a junction of multiple blood vessels;
rotating the shaft and the elongate clot engagement element about the principal longitudinal axis such that the end formation faces a selected blood vessel;
advancing the clot removal device along the selected blood vessel to encircle the clot from the proximal side of the clot location; and
withdrawing the clot removal device from the blood vessel.

18. A method of removing a clot from a blood vessel, the method comprising:
deploying a clot removal device into the blood vessel on a proximal side of a clot location, wherein the clot removal device comprises:
a shaft;
a clot capture element;
a sheath surrounding the clot capture element; and an elongate clot engagement element surrounded by the clot capture element,
  wherein the elongate clot engagement element is configured for deployment to the clot location from the proximal side of the clot location, the elongate clot engagement element having one end connected to the shaft and a distal end remote from the end connected to the shaft, and
  wherein the elongate clot engagement element is configured to avoid a central region of the clot and to engage the clot about a periphery of the clot,
wherein the shaft and the elongate clot engagement element have a principal longitudinal axis,
wherein the clot capture element and the elongate clot engagement element are expandable, the sheath being configured to control a rate of expansion of the clot capture element and the elongate clot engagement element, wherein the sheath is retractable, in a direction away from the distal end of the elongate clot engagement element, at a rate that controls the expansion rate of the clot capture element and the elongate clot engagement element,
wherein the elongate clot engagement element extends along a curved path defining a helix, and wherein the curved path defining the helix has an open end on a distal side thereof configured to encircle the clot from the proximal side of the clot location, with the distal end of the elongate clot engagement element being located substantially at the open end of the curved path defining the helix to define a substantially unobstructed channel on the clot removal device for encircling the clot from the proximal side of the clot location,
  wherein the distal end of the elongate clot engagement element comprises an end formation forming a leading curved contact surface, the end formation being displaced from the principal longitudinal axis to steer the clot removal device to advance through a blood vessel, and
  wherein the end formation is both displaced to one side of the substantially unobstructed channel for encircling the clot from the proximal side of the clot location and displaced from the curved path defining the helix;
advancing the clot removal device in the blood vessel to a junction of multiple blood vessels;
rotating the shaft and the elongate clot engagement element about the principal longitudinal axis such that the end formation faces a selected blood vessel;
advancing the clot removal device along the selected blood vessel to encircle the clot from the proximal side of the clot location; and
withdrawing the clot removal device from the blood vessel.

* * * * *